United States Patent
Wallin

[19]

[11] Patent Number: 6,155,256

[45] Date of Patent: Dec. 5, 2000

[54] FRESH GAS SYSTEM AND A METHOD FOR VAPORIZING A LIQUID ANAESTHETIC

[75] Inventor: Sten Wallin, Hägersten, Sweden

[73] Assignee: Siemens Elema AB, Sundyberg, Sweden

[21] Appl. No.: 09/189,678

[22] Filed: Nov. 13, 1998

[30] Foreign Application Priority Data

Dec. 15, 1997 [SE] Sweden ................................ 9704661

[51] Int. Cl.$^7$ ................................................ A61M 15/00
[52] U.S. Cl. .............................. 128/203.16; 128/203.12; 128/203.25; 128/204.23
[58] Field of Search .................... 128/203.16, 203.12, 128/204.21, 204.23, 204.18, 203.25, 203.14

[56] References Cited

U.S. PATENT DOCUMENTS

| | | | |
|---|---|---|---|
| 4,345,612 | 8/1982 | Koni et al. . | |
| 4,576,159 | 3/1986 | Hahn et al. . | |
| 5,423,313 | 6/1995 | Olsson et al. | 128/204.21 |
| 5,509,406 | 4/1996 | Kock et al. | 128/203.14 |
| 5,522,381 | 6/1996 | Olsson et al. | 128/203.12 |
| 5,575,283 | 11/1996 | Sjoestrand | 128/204.23 |
| 5,649,531 | 7/1997 | Heinonen . | |
| 5,701,888 | 12/1997 | Tham et al. | 128/204.21 |
| 5,743,253 | 4/1998 | Castor et al. | 128/200.24 |
| 5,771,882 | 6/1998 | Psaros et al. | 128/203.12 |
| 5,918,595 | 7/1999 | Olsson et al. | 128/203.26 |

FOREIGN PATENT DOCUMENTS 0 496 336  7/1992  European Pat. Off. .

OTHER PUBLICATIONS

Operating Manual for Halothane Vaporizer 950, Enflurane Vaporizer 951, Isoflurane Vaporizer 952, Siemens–Elema AB (1988).

Primary Examiner—John G. Weiss
Assistant Examiner—V. Srivastava
Attorney, Agent, or Firm—Hill & Simpson

[57] ABSTRACT

In a fresh gas system and a method for vaporizing a liquid anaesthetic in an anaesthetic machine, a gas preparation unit prepares a flow of fresh gas having a gas mixture from at least two sources of gas, the gas mixture is passed through a vaporizer where it picks up a quantity of anaesthetic related to the viscosity of the gas mixture. A control device controls the gas preparation unit. An arrangement is connected upstream from the vaporizer and is connected to the control device, for determining the composition of the gas mixture. The control device compensates the fresh gas system for the gas mixture's composition so that a specific amount of anaesthetic is always picked up by the gas mixture, regardless of the mixture's composition.

11 Claims, 2 Drawing Sheets

FRESH GAS SYSTEM AND A METHOD FOR VAPORIZING A LIQUID ANAESTHETIC

BACKGROUND OF THE INVENTION

1. Field of the Invention

The present invention is directed to a fresh gas system and a to method for vaporizing a liquid anaesthetic wherein a fresh flow of a gads mixture is passed through a liquid anaesthetic vaporizer to add the anaesthetic to the gas mixture.

2. Description of the Prior Art

The user manual "Halothane Vaporizer 950/Enflurane Vaporizer 951/Isoflurane Vaporizer 952", Siemens-Elema AB, October 1992, describes a vaporizer for a fresh gas system in an anaesthetic machine. Two gases, such as oxygen and air or oxygen and nitrous oxide, are mixed in a gas mixer and passed in a series of pulses, or as a continuous flow, through the vaporizer. A throttle is arranged in the vaporizer. A drop in pressure occurs when the gas mixture passes through the throttle. This drop in pressure affects the surface of a liquid anaesthetic in a chamber connected to the flow pathway, upstream from the throttle. The liquid anaesthetic is then forced through a capillary tube and is sprayed into the gas mixture downstream from the throttle where the liquid is vaporized. The throttle is adjustable for the uptake of different amounts of liquid anaesthetic so the fresh gas can be given different specific end concentrations of the anaesthetic. The throttle is calibrated for a specific gas pressure and for a specific gas mixture.

A disadvantage of this known system is that different gas mixtures have respective different viscosities, and this causes variations in the effect of the drop in pressure across the throttle. The variation can be up to about 10% from one mixture to another.

The same problem exists in other types of vaporizers, especially in vaporizer types in which some of the gas mixture is diverted with the aid of a drop in pressure.

SUMMARY OF THE INVENTION

An object of the present invention is to provide a fresh gas system, which avoids the aforesaid problems.

Another object of the present invention is to provide a method for the vaporization of liquid anaesthetics that avoids the aforesaid problems.

The above object is achieved in accordance with the principles of the present invention in a fresh gas system for use in an anesthetic machine, having a gas preparation unit wherein a flow of fresh gas is prepared, as a gas mixture from at least two sources of gas, the fresh gas system also having a vaporizer through which the gas mixture is passed so as to pick up a quantity of anesthetic, this quantity being dependent on the viscosity of the gas mixture, and a control device which controls the gas preparation unit, and an arrangement for determining the composition of the gas mixture disposed upstream from the vaporizer and connected to the control device, the control device receiving signals from this arrangement and compensating the fresh gas system dependent on the composition of the gas mixture so that a predetermined amount of anesthetic is always picked up by the gas mixture in the vaporizer, independently of the composition of the gas mixture.

By using an arrangement for identifying the composition of different gas mixtures, the fresh gas system can be compensated for the difference in viscosity for different gas mixtures. One such arrangement can be a setting device for the gas mixture's composition, i.e. the setting device the operator uses for selecting the gases, e.g. oxygen and air, or oxygen and nitrous oxide, in the gas mixture and the concentration of the respective gases.

A gas analyzer, arranged to analyze the gas mixture before it is fed into the vaporizer, is another example of such an arrangement means for identifying composition.

A third arrangement for identifying composition is a number of flow meters for measuring the respective partial flows of gas from the respective gas sources.

Compensation can be accomplished by regulation of the amount of liquid anaesthetic introduced into the gas flow or regulation of the flow itself. Compensating for the viscosity of the gas mixture by varying the amplitude of the flow of pulses of gas to the vaporizer is particularly advantageous with vaporizers of the aforesaid type.

The duration of pulses in conjunction with the latter form of compensation should be varied such that the volume of gas remains constant in each gas pulse.

In a method for the vaporization of a liquid anesthetic in accordance with the invention, a fresh flow of a gas mixture is generated and is passed through a vaporizer in order to pick up a quantity of anesthetic, this quantity being related to the viscosity of the gas mixture, and the method includes the steps of determining the composition of the gas mixture and compensating the generation of the gas flow of the gas mixture dependent on the composition of the mixture.

DESCRIPTION OF THE PREFERRED EMBODIMENTS

Figure 1:
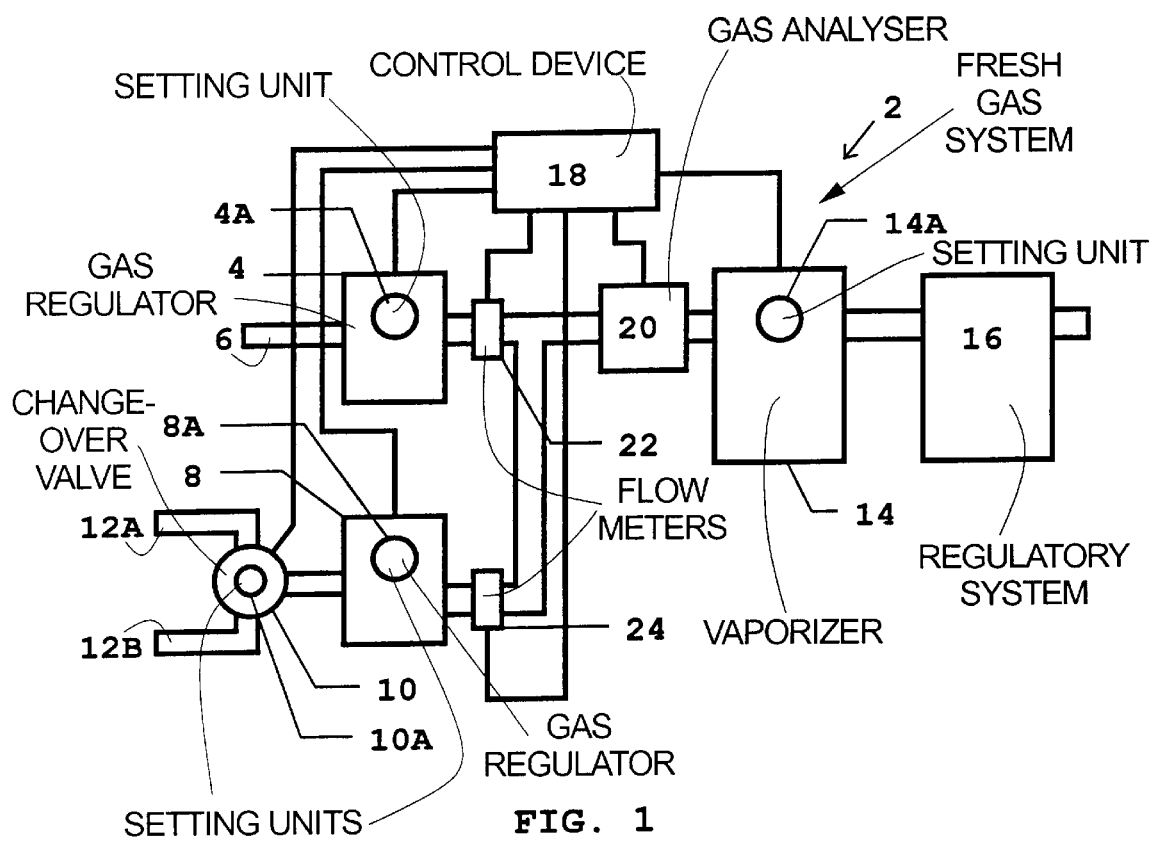
FIG. 1 is a block diagram of an embodiment of a fresh gas system constructed and operating in accordance with the invention.

FIG. 1 is a block diagram of an embodiment of a fresh gas system 2 according to the invention. The fresh gas system 2 includes a first gas regulator 4, preferably a valve, with a setting unit 4A for setting the flow of a first gas from a first gas connector 6. The first gas is suitably oxygen. A second or a third gas can be regulated by a second gas regulator 8 with a setting unit 8A, depending on the setting of a changeover valve 10. The changeover valve 10 also has a setting unit 10A. A second gas connector 12A is connected to the second gas regulator 8 when the changeover valve 10 is in a first position, and a third gas connector 12B is connected to the second gas regulator 8 when the changeover valve 10 is in a second position. The second gas can be air, and the third gas can be nitrous oxide.

A gas mixture consisting of oxygen and air, or oxygen and nitrous oxide, is prepared for the anaesthetization of a patient. The exact composition of the gas mixture is selected by the operator with the setting means 4A, 8A, 10A. Alternatively, settings can be made on an instrument panel (not shown) for the entire anaesthetic machine. In such a case, the setting units 4A, 8A, 10A correspond to the mechanical control elements that implement the settings in the subsystems.

The gases are mixed and then fed into a vaporizer 14 with a setting unit 14A. The gas mixture is enriched in the vaporizer 14 with an anaesthetic and is then sent to a regulatory system 16 for delivery to a patient circuit in the anaesthetic machine. The regulatory system 16 can have a gas reservoir for fresh gas, a regulatory valve, flow meters etc.

The vaporizer 14 can be a Halothane Vaporizer 950, an Enflurane Vaporizer 951 or an Isoflurane Vaporizer 952, as described in the introduction.

A control device 18 controls the fresh gas system 2. The control device 18 is connected to most of the components, and receives signals from them and emits control signals to them. In particular, the control device 18 selects appropriate compensation for variations in the viscosity of different gas mixture compositions.

In order to compensate for the gas mixture's composition, the control device 18 must receive information as to the contents of the mixture. The fresh gas system 2 therefore has at least one arrangement for determining the composition of the gas mixture. In principle, a first such arrangement has already been described, viz, the setting unit 4A, 8A, 10A. When the values for settings are sent to the control device 18, the device can determine an appropriate compensation for the viscosity of the composition which has been set.

Alternatively, or as a complement, a gas analyzer 20 can be arranged upstream from the vaporizer 14. The gas analyzer 20 analyzes the composition of the gas mixture and sends the results of the analysis to the control device 18. This solution is appropriate when gas delivery to the vaporizer 14 is largely continuous or when compensation is performed in the vaporizer 14.

Another alternative, or complement, is also shown in FIG. 1. A first flow meter 22 and a second flow meter 24 measure the respective gas flows from the various gas connectors 6, 12A/12B. The control device 18 can decide on a compensation from information on flow rates and gas fed to the second gas regulator B. This solution is also more appropriate when gas delivery to the vaporizer 14 is continuous or when compensation is performed in the vaporizer 14.

Figure 2:
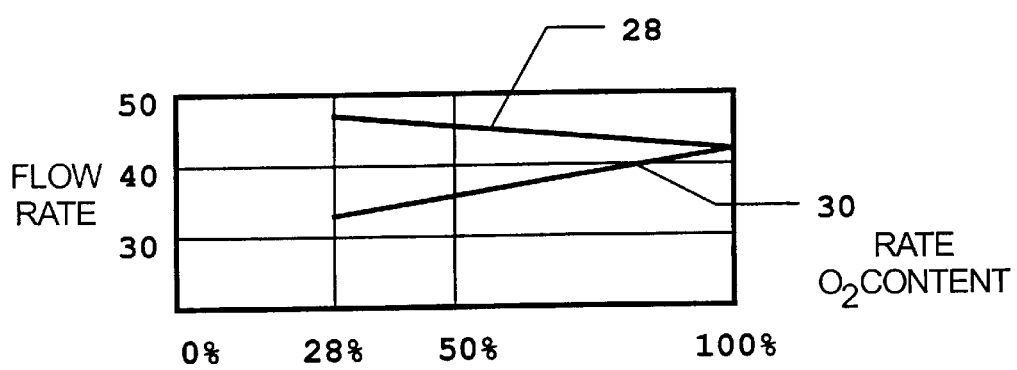
FIG. 2 is a diagram illustrating compensation dependent on the gas mixture's viscosity in accordance with the invention.
Figure 3:
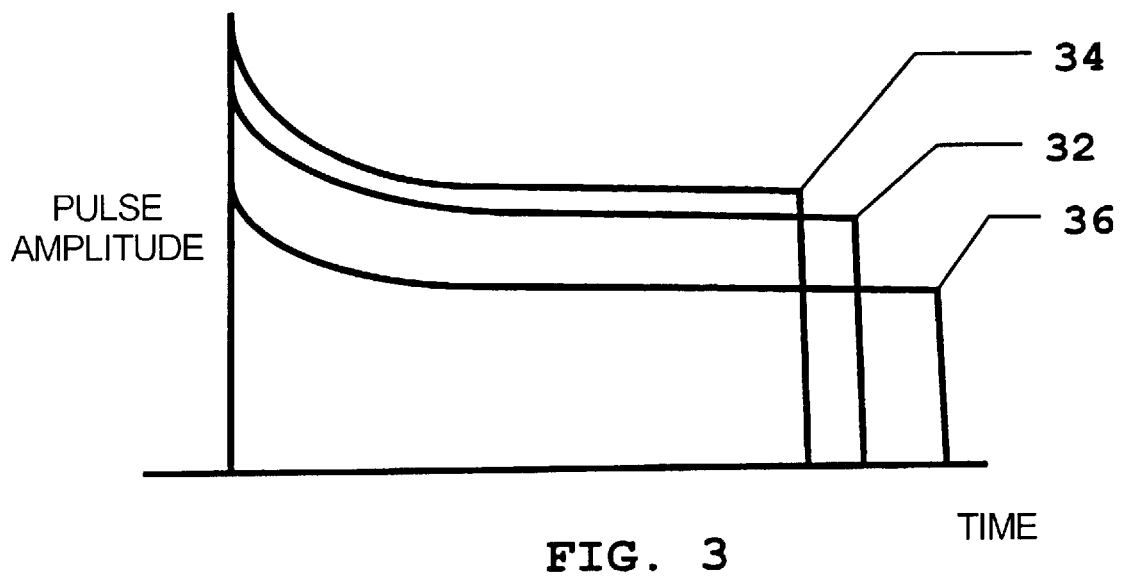
FIG. 3 is a diagram showing advantageous embodiments of pulses of the gas mixture used in the invention.

In the present embodiment of the fresh gas system 2, compensation occurs in the gas regulators 4, 8. Compensation is described below with simultaneous reference to all the figures. The gas regulators 4, 8 send pulsed flows 32, 34, 36 (FIG. 3) to the vaporizer 14. Each flow pulse 32 then serves as a basic pulse for which the vaporizer 14 is calibrated. The flow pulse 34 represents a compensated flow pulse for a gas mixture with a lower viscosity, according to line 28 in FIG. 2. Line 28 depicts linear compensation with an increasing flow rate as the oxygen content in a mixture with air declines (reading the graph in FIG. 2 from right to left). The faster flow is generated to achieve a greater drop in pressure in the vaporizer 14, thereby achieving delivery of the same amount of liquid anaesthetic as with the basic pulse 32. The duration of the flow pulse 34 is reduced so a predetermined volume is maintained.

In a corresponding manner, the flow pulse 36 illustrates compensation through a reduction in the flow rate. This takes place according to line 30, which represents a mixture of oxygen and nitrous oxide. Here, duration is instead prolonged so the same volume is achieved as with the basic pulse 32.

Compensation eliminates virtually all of the effect of viscosity on the end concentration of the anaesthetic, and the result is more accurate dispensing of anaesthetic.

Instead of compensating for the mixture's composition by varying the amplitude of flow, direct regulation can be achieved in the vaporizer 14, for example, by regulating the throttle in such a way that the drop in pressure across it compensates for the gas mixture's composition.

Although modifications and changes may be suggested by those skilled in the art, it is the intention of the inventor to embody within the patent warranted hereon all changes and modifications as reasonably and properly come within the scope of his contribution to the art.

I claim as my invention:

1. A fresh gas system for use in an anaesthetic machine, said fresh gas system comprising:

at least two gas sources containing respectively different gases;

a gas preparation unit connected to said at least two gas sources for preparing a flow of fresh gas comprising a gas mixture of at least said two different gases, said gas mixture having a unique viscosity;

a vaporizer in communication with said gas preparation unit, through which said gas mixture is passed, said gas mixture in said vaporizer picking up a quantity of anaesthetic dependent on the viscosity of said gas mixture;

means for determining a composition of said gas mixture disposed upstream from said vaporizer and for emitting a signal identifying said composition; and control means, supplied with said signal, for controlling said gas preparation unit for compensating for the composition of the gas mixture for causing a predetermined amount of anaesthetic to be picked up by said gas mixture in said vaporizer independently of the composition of said mixture.

2. A fresh gas system as claimed in claim 1 wherein said means for determining the composition of the gas mixture comprises setting means for setting the composition of the gas mixture.

3. A fresh gas system as claimed in claim 1 wherein said means for determining the composition of the gas mixture comprises a gas analyzer.

4. A fresh gas system as claimed in claim 1 wherein said means for determining the composition of the gas mixture comprises at least two flow meters respectively connected for measuring the respective flows of the respective different gases from said at least two gas sources.

5. A fresh gas system as claimed in claim 1 wherein said vaporizer comprises means for releasing anaesthetic into said gas mixture dependent on a drop in pressure across said vaporizer, and wherein said gas preparation unit generates said flow of fresh gas as a plurality of pulses of said fresh gas at a predetermined flow amplitude, and wherein said control means comprises means for controlling said gas preparation unit to vary the amplitude of the pulses for compensating for the composition of the gas mixture.

6. A fresh gas system as claimed in claim 5 wherein said control means comprises means for controlling the gas preparation unit to vary a duration of the pulses for maintaining a constant volume of said fresh gas.

7. A fresh gas system as claimed in claim 5 wherein one of said different gases comprises oxygen, and wherein said gas mixture has an oxygen content, and wherein said control means comprises means for linearly compensating the amplitude of the pulses of said fresh gas dependent on said oxygen content of said gas mixture.

8. A fresh gas system as claimed in claim 1 wherein said at least two gas sources include an oxygen source and a nitrous oxide source, and wherein said gas preparation unit comprises a first valve for regulating a flow of oxygen from said oxygen source and a second valve for regulating a flow of nitrous oxide from said nitrous oxide source.

9. A fresh gas system as claimed in claim 1 wherein said at least two gas sources include an oxygen source and an air source, and wherein said gas preparation unit comprises a first valve for regulating a flow of oxygen from said oxygen source and a second valve for regulating a flow of air from said air source.

10. A method for vaporizing a liquid anaesthetic comprising the steps of:

generating a fresh flow of a gas mixture, said gas mixture having a composition and a unique viscosity dependent on said composition;

passing said gas mixture through a vaporizer, said gas mixture picking up a quantity of anaesthetic in said vaporizer dependent on the viscosity of said gas mixture;

identifying the composition of said gas mixture; and compensating the generation of the fresh flow of the gas mixture dependent on the composition of the mixture for causing said gas mixture to pick up a predetermined quantity of anaesthetic in said vaporizer independently of said composition.

11. A method as claimed in claim 10 wherein the step of generating said fresh flow of a gas mixture comprises generating said fresh flow of a gas mixture as a plurality of pulses with a predetermined flow amplitude, and wherein the step of compensating comprises linearly compensating for changes in the flow amplitude.

* * * * *